United States Patent
Wang et al.

(10) Patent No.: US 8,691,720 B2
(45) Date of Patent: Apr. 8, 2014

(54) PROCESS FOR DEHYDROCHLORINATING 1,1,1,2-TETRAFLUORO-2-CHLOROPROPANE TO 2,3,3,3-TETRAFLUOROPROPENE IN THE PRESENCE OF AN ALKALI METAL-DOPED MAGNESIUM OXYFLUORIDE CATALYST AND METHODS FOR MAKING THE CATALYST

(75) Inventors: Haiyou Wang, Amherst, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 63 days.

(21) Appl. No.: 13/271,425

(22) Filed: Oct. 12, 2011

(65) Prior Publication Data

US 2012/0129687 A1    May 24, 2012

Related U.S. Application Data

(62) Division of application No. 12/472,787, filed on May 27, 2009, now Pat. No. 8,053,612.

(60) Provisional application No. 61/057,477, filed on May 30, 2008.

(51) Int. Cl.
*C07C 17/23* (2006.01)

(52) U.S. Cl.
USPC .......................................... 502/224; 570/156

(58) Field of Classification Search
None
See application file for complete search history.

(56) References Cited

U.S. PATENT DOCUMENTS

| 5,986,151 | A | * | 11/1999 | Van Der Puy | 570/175 |
| 6,031,141 | A | * | 2/2000 | Mallikarjuna et al. | 570/136 |
| 7,026,520 | B1 | * | 4/2006 | Mukhopadhyay et al. | 570/123 |
| 7,189,884 | B2 | | 3/2007 | Mukhopadhyay et al. | |
| 2005/0090698 | A1 | | 4/2005 | Merkel et al. | |
| 2009/0018375 | A1 | * | 1/2009 | Nappa | 570/156 |

FOREIGN PATENT DOCUMENTS

| EP | 2066605 A2 | 6/2009 |
| WO | 2007/117391 | 10/2007 |

* cited by examiner

*Primary Examiner* — Melvin C Mayes
*Assistant Examiner* — Colette Nguyen
(74) *Attorney, Agent, or Firm* — Bruce O. Bradford

(57) ABSTRACT

A process for making a fluorinated olefin and/or catalyst composition. The process has the step of dehydrochlorinating a hydrochlorofluorocarbon having at least one hydrogen atom and at least one chlorine atom on adjacent carbon atoms in the presence of a catalytically effective amount of a catalyst composition. The catalyst composition is represented by the following: n wt. % $MX/M'O_yF_z$, wherein $0<y<1$ and $0<z<2$ and wherein $y+z/2=1$; M is an alkali metal ion selected from the group consisting of $Li^+$, $Na^+$, $K^+$, $Rb^+$, and $Cs^+$; X is a halogen ion selected from the group consisting of $F^-$, $Cl^-$, $Br^-$, and $I^-$, M' is a bivalent metal ion; wherein n is a weight percentage of about 0.05% to about 50% MX based on the total weight of the MX and $M'O_yF_z$, and wherein y and z are the mole fractions of oxygen and fluorine in $M'O_yF_z$, respectively.

18 Claims, No Drawings

PROCESS FOR DEHYDROCHLORINATING 1,1,1,2-TETRAFLUORO-2-CHLOROPROPANE TO 2,3,3,3-TETRAFLUOROPROPENE IN THE PRESENCE OF AN ALKALI METAL-DOPED MAGNESIUM OXYFLUORIDE CATALYST AND METHODS FOR MAKING THE CATALYST

CROSS-REFERENCE TO A RELATED APPLICATION

This application is a Divisional of U.S. application Ser. No. 12/472,787, filed May 27, 2009 (now U.S. Pat. No. 8,053,612), which claims priority benefit of U.S. Provisional Application No. 61/057,477, filed May 30, 2008, each of which are incorporated herein by reference.

BACKGROUND OF THE INVENTION

1. Field of the Invention

The present invention relates to a process for dehydrochlorinating 1,1,1,2-tetrafluoro-2-chloropropane (244bb) in the presence of a catalyst to make 2,3,3,3-tetrafluoropropene (1234yf). The present invention further relates to two methods for making an alkali metal-doped magnesium oxyfluoride catalyst.

2. Description of the Related Art

Chlorine-containing compounds, such as chlorofluorocarbons (CFCs), have been employed as refrigerants, foam blowing agents, cleaning agents, solvents, heat transfer media, sterilants, aerosol propellants, dielectrics, fire extinguishing agents, and power-cycle working fluids. Such chlorine-containing compounds may be detrimental to the Earth's ozone layer. Further, many of the hydrofluorocarbons (HFCs) used as the substitutes for CFCs, have also been found to contribute to global warming. For these reasons, there is a need to develop new compounds that are more environmentally benign. 2,3,3,3-tetrafluoropropene (1234yf), a compound with low global warming potential (GWP), is one such environmentally benign compound.

1234yf can be produced by dehydrochlorination of 1,1,1,2-tetrafluoro-2-chloropropane (244bb), a CFC. It would be desirable to have a catalyst system that affords a high degree of conversion and/or selectivity in such a reaction. It would be further desirable to have a catalyst system that was analogously useful in other dehydrochlorination processes for converting CFCs to HFCs.

SUMMARY OF THE INVENTION

According to the present invention, there is a process for making a fluorinated olefin. The process has the step of dehydrochlorinating a hydrochlorofluorocarbon having at least one hydrogen atom and at least one chlorine atom on adjacent carbon atoms in the presence of a catalytically effective amount of a catalyst composition. The catalyst composition is represented by the following: n wt. % $MX/M'O_yF_z$, wherein $0<y<1$ and $0<z<2$ and wherein $y+z/2=1$; M is an alkali metal ion selected from the group consisting of $Li^+$, $Na^+$, $K^+$, $Rb^+$, and $Cs^+$; X is a halogen ion selected from the group consisting of $F^-$, $Cl^-$, $Br^-$, and $I^-$, M' is a bivalent metal ion; wherein n is a weight percentage of about 0.05% to about 50% MX based on the total weight of the MX and $M'O_yF_z$, and wherein y and z are the mole fractions of oxygen and fluorine in $M'O_yF_z$, respectively.

Further according to the present invention, there is a method for preparing a solid catalyst composition. The method has the following steps: (A) dissolving (i) an alkali metal halide in an effective amount of solvent or (ii) one or more of a hydroxide, an oxide, or a carbonate of an alkali metal in an aqueous solution of a hydrogen halide to form an alkali metal halide solution; (B) admixing an effective amount of a bivalent metal oxyfluoride in the alkali metal halide solution to form a slurry and optionally extruding the slurry to form an extrudate; (C) substantially removing the solvent from the slurry or the extrudate to form a solid residue; (D) calcining the solid residue composition at conditions sufficient to effect substantial calcination; (E) grinding the calcined sample into fine powder, and (F) pelletizing said fine powder to form pellets of the catalyst composition.

Further according to the present invention, there is another method for preparing the catalyst composition. The method has the following steps: (A) dissolving (i) an alkali metal halide in an effective amount of solvent or (ii) one or more of a hydroxide, an oxide, or a carbonate of an alkali metal in an aqueous solution of a hydrogen halide to form an alkali metal halide solution; (B) admixing one or more of a hydroxide, an oxide, or a carbonate of a bivalent metal with the alkali metal halide solution to form a slurry; (C) substantially removing the solvent from the slurry to form a solid residue of the alkali metal halide and the one or more of the hydroxide, the oxide, or the carbonate of the bivalent metal; (D) calcining the solid residue composition at conditions sufficient to effect substantial calcination; (E) grinding the calcined sample into fine powder, (F) pelletizing said fine powder to form pellets; and (G) contacting the pellets with HF under conditions sufficient to convert the one or more of a hydroxide, an oxide, or a carbonate of a bivalent metal to a bivalent metal oxyfluoride to form pellets of the catalyst composition.

DETAILED DESCRIPTION OF THE INVENTION

The process of the present invention is useful for making fluorinated olefins. A hydrochlorofluorocarbon having at least one hydrogen atom and at least one chlorine atom on adjacent carbon atoms is dehydrochlorinated in the presence of a catalytically effective amount of a catalyst composition. The catalyst composition is represented by the following:

$$n \text{ wt. \% } MX/M'O_yF_z$$

"n" represents the weight percentage of MX in the catalytic composition based on the total weight of the MX and $M'O_yF_z$. The weight percentage preferably ranges from about 0.05% to about 50%, more preferably from about 5% to about 15%, and most preferably from about 7.5% to about 12.5%.

"MX" refers to an alkali metal halide. "M" is an alkali metal ion selected from the group consisting of $Li^+$, $Na^+$, $K^+$, $Rb^+$, and $Cs^+$. Preferred alkali metal ions include $K^+$ and $Cs^+$. "X" is a halogen ion selected from the group consisting of $F^-$, $Cl^-$, $Br^-$, and $I^-$. Preferred halogen ions include $F^-$ and $Cl^-$. Examples of alkali metal halides include LiCl, NaCl, KCl, CsCl, LiF, NaF, KF, and CsF.

"$M'O_yF_z$" refers to a bivalent metal oxyfluoride. M' is a bivalent metal ion. Useful bivalent metal ions include $Mg^{2+}$, $Ca^{2+}$, $Ni^{2+}$, $Fe^{2+}$, $Co^{2+}$, $Cu^{2+}$, and $Zn^{2+}$. Preferred bivalent metal ions include $Mg^{2+}$ and $Ni^{2+}$. "y" and "z" represent mole fractions of oxygen and fluorine in $M'O_yF_z$, respectively, and are $0<y<1$ and $0<z<2$ and wherein $y+z/2=1$. Examples of bivalent metal oxyfluorides include oxyfluorides of Mg, Ni, Co, Cu, and Zn.

In a preferred catalyst composition, "n" is about 10%, M is selected from among $Na^+$, $K^+$ and $Cs^+$, X is selected from among $F^-$, $Cl^-$, and $Br^-$, and M' is selected from $Mg^{2+}$ and $Ni^{2+}$. In another preferred catalyst composition, "n" is about 10%, M is selected from among $K^+$ and $Cs^+$. X is selected from among $F^-$ and $Cl^-$. M' is selected from among $Mg^{2+}$ and $Ni^{2+}$.

The process of the present invention is useful for making fluorinated olefins via dehydrochlorination of hydrochlorofluorocarbons having at least one hydrogen atom and at least one chlorine atom on adjacent carbon atoms. Table 1 lists hydrochlorofluorocarbons and their corresponding fluorinated olefin products.

TABLE 1

| Hydrochlorofluorocarbon | Fluorinated olefin |
|---|---|
| $CF_3CFClCH_3$ (244bb) | $CF_3CF=CH_2$ (1234yf) |
| $CF_3CHFCH_2Cl$ (244eb) | $CF_3CF=CH_2$ (1234yf) |
| $CF_3CH_2CHFCl$ (244fa) | $CF_3CH=CHF$ (trans/cis-1234ze) |
| $CF_3CHClCH_2F$ (244db) | $CF_3CH=CHF$ (trans/cis-1234ze) |
| $CF_3CFClCH_2F$ (235bb) | $CF_3CF=CHF$ (Z/E-1225ye) |
| $CF_3CHFCHFCl$ (235ea) | $CF_3CF=CHF$ (Z/E-1225ye) |
| $CF_3CH_2CF_2Cl$ (235fa) | $CF_3CH=CF_2$ (1225zc) |
| $CF_3CHClCHF_2$ (235da) | $CF_3CH=CF_2$ (1225zc) |
| $CF_3CFClCHF_2$ (226ba) | $CF_3CF=CF_2$ (1216) |

A preferred hydrochlorofluorocarbon is 1,1,1,2-tetrafluoro-2-chloropropane (244bb), and the corresponding fluorinated olefin product is 2,3,3,3-tetrafluoropropene (1234yf).

In addition to the fluorinated olefin, i.e., the hydrofluorocarbon or fluorocarbon, the product mixture may also have unconverted hydrochlorofluorocarbon and by-product hydrogen chloride.

Enhanced or improved selectivity for the target product is an important feature of the present invention. The dehydrochlorination reaction is preferably carried out at a selectivity of about 50% or more, preferably about 70% or more, and most preferably about 90% or more. Conversion is preferably about 5% or more and most preferably about 20% or more.

Dehydrochlorination may be carried out at a temperature range of about 200° C. to about 800° C., preferably from about 300° C. to about 600° C., and more preferably from about 350° C. to about 500° C. in the presence of a catalyst. It is contemplated that a variety of reaction pressures may be used, such as superatmospheric, atmospheric, and subatmospheric.

Dehydrochlorination may optionally be carried out in presence or absence of an oxidizing agent. Useful examples of oxidizing agents include, but are not limited to, oxygen and carbon dioxide. Use of an oxidizing agent can extend the life of the catalyst. The oxidizing agent can be pure or diluted with an inert gas such as nitrogen before being introduced into reactor. The level of oxidizing agent is generally from about 1% to about 10% by volume and preferably from about 2% to 5% by volume based on the volume of the organic feed.

It may also be advantageous to periodically regenerate the catalyst after prolonged use while in place in the reactor. Regeneration of the catalyst may be accomplished by any means known in the art. One method is by passing oxygen or oxygen diluted with nitrogen over the catalyst at temperatures of about 200° C. to about 600° C. (preferably about 350° C. to about 450° C.) for about 0.5 hour to about 3 days followed by halogenation treatment at temperatures of about 25° C. to about 600° C. (preferably about 200° C. to about 400° C.).

Dehydrochlorination is preferably carried out in a corrosion-resistant reaction vessel. Examples of corrosion-resistant materials are Hastelloy, Inconel, and Monel. The vessel may have a fixed or a fluidized catalyst bed. If desired, inert gases such as nitrogen or argon may be employed in the reactor during operation.

The catalyst composition can be prepared according to a method (a first method) of the present invention. The method has the following steps: (A) dissolving (i) an alkali metal halide in an effective amount of solvent or (ii) one or more of a hydroxide, an oxide, or a carbonate of an alkali metal in an aqueous solution of a hydrogen halide to form an alkali metal halide solution; (B) admixing an effective amount of a bivalent metal oxyfluoride in the alkali metal halide solution to form a slurry; (C) substantially removing the solvent from the slurry to form a solid residue; (D) calcining the solid residue composition at conditions sufficient to effect substantial calcination; (E) grinding the calcined sample into fine powder, and (F) pelletizing said fine powder to form pellets of the catalyst composition.

The catalyst composition can be prepared according to another method (a second method) of the present invention. The method has the following steps: (A) dissolving (i) an alkali metal halide in an effective amount of solvent or (ii) one or more of a hydroxide, an oxide, or a carbonate of an alkali metal in an aqueous solution of a hydrogen halide to form an alkali metal halide solution; (B) admixing one or more of a hydroxide, an oxide, or a carbonate of a bivalent metal in the alkali metal halide solution to form a slurry; (C) substantially removing the solvent from the slurry to form a solid residue of the alkali metal halide and the one or more of the hydroxide, the oxide, or the carbonate of the bivalent metal; (D) calcining the solid residue composition at conditions sufficient to effect substantial calcination; (E) grinding the calcined sample into fine powder, (F) pelletizing said fine powder to form pellets; and (G) contacting the pellets with HF under conditions sufficient to convert the one or more of the hydroxide, the oxide, or the carbonate of the bivalent metal to a bivalent metal oxyfluoride.

The solvent selected will be one in which the alkali metal halide will readily dissolve. The particular solvent used may depend on the selection of alkali metal halide. Solvents useful in the present invention include, but are not limited to, water, alcohols (monohydric and polyhydric) and ethers. Preferred alcohols have one to five carbons. Water is the most preferred solvent. The bivalent metal oxyfluoride can be added directly to the alkali metal halide/solvent mixture (admixed with) or be premixed in a quantity of the same solvent used for the alkali metal halide and the premix added directly to the alkali metal halide/solvent mixture.

In either of the two methods described above, the solvent is preferably removed by driving off a portion of the solvent from the slurry to form a paste (moldable mass) and drying the paste to form a powder. The solvent is preferably driven off by any conventional method known in the art, such as vigorous stirring at ambient or elevated temperatures, evaporation, settling and decanting, centrifugation, or filtration, such that a paste is formed. The paste is then preferably dried by any known conventional means, e.g., by oven heating, spray drying, or evaporation, to form a substantially free-flowing powder. The solvent is removed such that the catalyst composition is less than 1 wt. %, preferably less than 0.5 wt %, more preferably less than 0.1 wt % solvent based on the total weight of the composition. Most preferably, the catalyst composition is substantially free of solvent after removal of the solvent.

After the solvent is removed, the solid residue is preferably calcined at conditions sufficient to effect substantial calcination. Calcination is preferably carried out at a temperature from about 300° C. to about 600° C. and more preferably about 400° C. to about 450° C. The calcination is preferably carried out in the presence of an inert gas, such as nitrogen or argon. The calcination is preferably carried out for a time period of about 2 hours to about 8 hours and more preferably about 4 hours to about 6 hours. The calcination may be carried out at a variety of pressures, such as superatmospheric, atmospheric, and subatmospheric. Atmospheric pressure is preferred.

After the solid residue is calcined, the calcined solid mass is ground to form a finely divided powder. The finely divided powder is then pelletized to a pellet form. If desired, excipients, such as lubricants and binders, may be added to the powder prior to pelletization.

In the second method, the pellets are contacted with HF under conditions sufficient to effect conversion of one or more of the hydroxide, oxide, or carbonate of the bivalent metal to the bivalent metal oxyfluoride. The conversion is carried out at a temperature of about 300° C. to about 600° C., preferably about 350° C. to about 550° C., and most preferably about 400° C. to about 500° C. The conversion is preferably carried out at atmospheric pressure. However, superatmospheric and subatmospheric pressures may be used if desired. The conversion is carried out for a time period of about 0.5 hours to about 20 hours, preferably about 1 hour to about 8 hours, and most preferably about 2 hours to about 4 hours.

The following are examples of the present invention, and are not to be construed as limiting.

EXAMPLES

The following examples demonstrate that selected bivalent metal oxyfluoride-based catalysts prepared by using the methods of the present invention are active and selective for the dehydrochlorination of 244bb to 1234yf and are more active than their counterpart bivalent metal fluoride-based catalysts.

Example 1

244bb Dehydrohalogenation Over HF-Treated 10 wt % CsCl/MgO Catalyst

In example 1, a 10 wt % CsCl/MgO$_y$F$_z$ catalyst was prepared by (a) dissolving 6.67 grams of 99.9% CsCl in 200 ml of water to form a CsCl aqueous solution; (b) admixing 60.00 grams of a MgO in the CsCl solution to form a slurry; (c) removing the water from the slurry by vigorously stirring at room temperature to 80° C. to form a paste; (d) drying the paste at 100° C. to 120° C. for 8 hours in an oven to form a solid residue; (e) calcining the solid residue at 400° C. under nitrogen for 4 hours; (f) grinding the calcined sample in a mortar and pestle to form a finely divided powder; and (f) pelletizing the powder to form pellets. 20 cc of the pellets was loaded into a ¾-inch Monel reactor and was treated with 5% HF/N$_2$ flow at 350-490° C. for 2 hours prior to reaction.

A mixture of 99.1%244bb/0.4%1233xf mole percent was then passed through the catalyst bed at a rate of 6 grams/hour (g/h). The temperature at the bottom of catalyst bed and that at the top of catalyst bed were recorded and reported. As shown in Table 2, the HF-treated 10 wt % CsCl/MgO catalyst provided a 244bb conversion of about 33% and a 1234yf selectivity of about 97%. Its activity was about 60% higher than that of the 10 wt % CsCl/MgF$_2$ catalyst under similar conditions.

TABLE 2

(reactivity of HF-treated 10 wt % CsCl/MgO during 244bb dehydrohalogenation and its comparison with 10 wt % CsCl/MgF$_2$ catalyst*)

| Catalyst | Temp. Bottom-Top (°) | t (h) | Conversion (%) 244bb | Selectivity (%) 1234yf | Selectivity (%) 1233xf | Selectivity (%) others |
|---|---|---|---|---|---|---|
| HF-treated 10 wt % CsCl/MgO** | 426-480 | 1 | 32.9 | 96.2 | 0.5 | 3.3 |
| | 424-481 | 2 | 33.5 | 96.1 | 0.6 | 3.3 |
| | 424-479 | 4 | 33.4 | 96.5 | 0.5 | 3.0 |
| | 424-479 | 6 | 34.2 | 96.6 | 0.5 | 2.9 |
| | 424-479 | 8 | 34.1 | 96.6 | 0.5 | 2.8 |
| | 424-478 | 10 | 34.2 | 96.9 | 0.5 | 2.6 |
| | 424-478 | 12 | 33.7 | 96.7 | 0.5 | 2.8 |
| | 424-478 | 14 | 33.0 | 96.7 | 0.5 | 2.8 |
| | 424-478 | 16 | 33.6 | 96.7 | 0.5 | 2.8 |
| | 424-478 | 18 | 33.6 | 96.7 | 0.5 | 2.8 |
| | 426-480 | 20 | 34.0 | 96.8 | 0.5 | 2.7 |
| | 426-480 | 22 | 34.6 | 96.8 | 0.5 | 2.7 |
| | 424-478 | 24 | 33.0 | 96.6 | 0.5 | 2.8 |
| 10 wt % CsCl/MgF$_2$* (comparative example) | 380-481 | 1 | 10.3 | 91.1 | 0.0 | 8.9 |
| | 380-481 | 2 | 14.0 | 95.9 | 0.0 | 4.1 |
| | 380-482 | 4 | 16.8 | 96.7 | 0.0 | 3.3 |
| | 380-484 | 6 | 19.6 | 97.4 | 0.0 | 2.6 |
| | 380-482 | 8 | 20.0 | 97.5 | 0.0 | 2.5 |
| | 380-481 | 10 | 20.5 | 97.5 | 0.0 | 2.5 |
| | 380-481 | 12 | 20.6 | 97.8 | 0.0 | 2.2 |
| | 380-479 | 14 | 19.9 | 97.7 | 0.0 | 2.3 |
| | 380-478 | 16 | 20.0 | 97.8 | 0.0 | 2.2 |
| | 380-481 | 18 | 21.0 | 97.8 | 0.0 | 2.2 |
| | 380-483 | 20 | 21.8 | 98.0 | 0.0 | 2.0 |
| | 380-481 | 22 | 20.7 | 97.7 | 0.0 | 2.3 |
| | 380-481 | 24 | 19.7 | 97.6 | 0.0 | 2.4 |

*Reaction conditions: 20 ml of catalyst, 6 g-organic/h, 99.1% 244bb/0.4% 1233xf, 1 atm;
**treated in 5% HF/N$_2$ flow (1400 ml/min) for 2 h at 350-490° C.

Example 2

244bb Dehydrohalogenation Over HF-Treated 10 wt % CsF/MgO Catalyst

In example 2, a 10 wt % CsF/MgO$_y$F$_z$ catalyst was prepared by (a) dissolving 6.67 grams of 99.9% CsF in 200 ml of water to form a CsF aqueous solution; (b) admixing 60.00 grams of a MgO in the CsF solution to form a slurry; (c) removing the water from the slurry by vigorously stirring at room temperature to 80° C. to form a paste; (d) drying the paste at 100° C. to 120° C. for 8 hours in an oven to form a solid residue; (e) calcining the solid residue at 400° C. under nitrogen for 4 hours; (f) grinding the calcined sample in a mortar and pestle to form a finely divided powder; and (f) pelletizing the powder to form pellets. 20 cc of the pellets was loaded into a ¾-inch Monel reactor and was treated with 5% HF/N$_2$ flow at 350-490° C. for 2 hours prior to reaction.

A mixture of 99.1%244bb/0.4%1233xf mole percent was then passed through catalyst bed at a rate of 6 g/h. The temperature at the bottom of catalyst bed and at the top of catalyst bed were recorded and reported. As shown in Table 3, the HF-treated 10 wt % CsF/MgO catalyst provided a 244bb conversion of about 28% and a 1234yf selectivity of about 98%. Its activity was about 40% higher than that of the 10 wt % CsF/Mg F$_2$ catalyst under similar conditions.

TABLE 3

(Reactivity of HF-treated 10 wt % CsF/MgO catalyst during 244bb dehydrohalogenation and its comparison with 10 wt % CsF/MgF$_2$ catalyst*)

| Catalyst | Temp. Bottom-Top (°) | t (h) | Conversion (%) 244bb | Selectivity (%) 1234yf | Selectivity (%) 1233xf | Selectivity (%) others |
|---|---|---|---|---|---|---|
| HF-treated 10 wt % CsF/MgO** | 415-480 | 1 | 23.4 | 96.9 | 0.3 | 2.8 |
| | 415-481 | 2 | 24.6 | 97.1 | 0.2 | 2.6 |
| | 416-479 | 4 | 25.7 | 97.4 | 0.2 | 2.4 |
| | 415-479 | 6 | 25.8 | 97.4 | 0.2 | 2.4 |
| | 415-480 | 8 | 27.1 | 97.5 | 0.2 | 2.3 |
| | 414-477 | 10 | 26.1 | 97.4 | 0.2 | 2.3 |
| | 415-481 | 12 | 27.4 | 97.5 | 0.2 | 2.2 |
| | 416-479 | 14 | 27.6 | 97.5 | 0.2 | 2.2 |
| | 413-475 | 16 | 26.0 | 97.4 | 0.3 | 2.3 |
| | 415-481 | 18 | 28.7 | 97.6 | 0.2 | 2.2 |
| | 416-479 | 20 | 27.9 | 97.6 | 0.2 | 2.2 |
| | 415-479 | 22 | 27.5 | 97.5 | 0.3 | 2.2 |
| | 416-476 | 24 | 26.5 | 97.5 | 0.3 | 2.2 |
| 10 wt % CsF/MgF$_2$* (comparative example) | 403-481 | 1 | 14.2 | 89.5 | 0.0 | 10.5 |
| | 403-481 | 2 | 14.1 | 91.8 | 0.0 | 8.2 |
| | 403-482 | 4 | 17.6 | 96.8 | 0.0 | 3.2 |
| | 403-481 | 6 | 20.6 | 97.4 | 0.0 | 2.6 |
| | 403-481 | 8 | 21.1 | 97.4 | 0.0 | 2.6 |
| | 403-481 | 10 | 21.4 | 97.6 | 0.0 | 2.4 |
| | 403-482 | 12 | 20.9 | 97.7 | 0.0 | 2.3 |
| | 403-482 | 14 | 20.8 | 97.7 | 0.0 | 2.3 |
| | 403-481 | 16 | 20.4 | 97.7 | 0.0 | 2.3 |
| | 403-480 | 18 | 20.4 | 97.6 | 0.0 | 2.4 |
| | 403-481 | 20 | 20.9 | 97.8 | 0.0 | 2.2 |
| | 403-481 | 22 | 21.0 | 97.7 | 0.0 | 2.3 |
| | 403-480 | 24 | 20.2 | 97.7 | 0.0 | 2.3 |

*Reaction conditions: 20 ml of catalyst, 6 g-organic/h, 99.1% 244bb/0.4% 1233xf, 1 atm;
**treated in 5% HF/N$_2$ flow (1400 ml/min) for 2 hours at 350-490° C.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method, comprising the following steps:
   (A) dissolving (i) an alkali metal halide in an effective amount of solvent or (ii) one or more of a hydroxide, an oxide, or a carbonate of an alkali metal in an aqueous solution of a hydrogen halide to form an alkali metal halide solution and
   (B) admixing an effective amount of a bivalent metal oxyfluoride in the alkali metal halide solution to form a slurry.

2. The method of claim 1, further comprising
   (C) substantially removing the solvent from the slurry to form a solid residue;
   (D) calcining the solid residue at conditions sufficient to effect substantial calcination; and
   (E) grinding the calcined residue into a powder; and
   (F) pelletizing the powder to form a solid catalyst composition.

3. The method of claim 1, further comprising
   (C) extruding the slurry to form an extrudate;
   (D) substantially removing the solvent from the extrudate to form a solid residue; and
   (E) optionally calcining the solid residue at conditions sufficient to effect substantial calcination.

4. The method of claim 2, wherein substantially removing the solvent comprises the following steps: driving off a portion of the solvent from the slurry or the extrudate to form a paste and drying the paste to form a powder.

5. The method of claim 2, wherein the solid residue is ground to form a finely divided powder; and wherein calcining is carried out at a temperature from about 300° C. to about 600° C.

6. The method of claim 2, wherein the catalyst composition is represented by the following:

$$n \text{ wt. } \% \text{ MX/M'O}_y\text{F}_z$$

wherein the alkali metal halide is represented by MX; wherein the bivalent metal oxyfluoride is represented by MX/M'O$_y$F$_z$; wherein 0<y<1 and 0<z<2 and wherein y+z/2=1; wherein M is an alkali metal ion selected from the group consisting of Li$^+$, Na$^+$, K$^+$, Rb$^+$, and Cs$^+$, X is a halogen ion selected from the group consisting of F$^-$, Cl$^-$, Br$^-$, and I$^-$, M' is a bivalent metal ion; wherein n is a weight percentage of about 0.05% to about 50% MX based on the total weight of the MX and M'O$_y$F$_z$, and wherein y and z are the mole fractions of oxygen and fluorine in M'O$_y$F$_z$, respectively.

7. The method of claim 6, the bivalent metal ion is selected from the group consisting of Mg$^{2+}$, Ca$^{2+}$, Sr$^{2+}$, Ba$^{2+}$, Ni$^{2+}$, Fe$^{2+}$, Co$^{2+}$, Cu$^{2+}$, and Zn$^{2+}$, and wherein the halogen ion is selected from the group consisting of F$^-$ and Cl$^-$.

8. The method of claim 6, wherein the bivalent metal ion is Mg$^{2+}$ or Ni$^{2+}$, wherein the alkali metal ion is Cs$^+$ or K$^+$, and wherein the halogen ion is selected from the group consisting of F$^-$ and Cl$^-$.

9. A method, comprising the following steps:
   (A) dissolving (i) an alkali metal halide in an effective amount of solvent or (ii) one or more of a hydroxide, an oxide, or a carbonate of an alkali metal in an aqueous solution of a hydrogen halide to form an alkali metal halide solution and
   (B) admixing one or more of a hydroxide, an oxide, or a carbonate of a bivalent metal in the alkali metal halide solution to form a slurry.

10. The method of claim 9, further comprising
    (C) substantially removing the solvent from the slurry to form a solid residue of the an alkali metal halide and the one or more of the hydroxide, the oxide, or the carbonate of the bivalent metal;
    (D) calcining the solid residue at conditions sufficient to effect substantial calcination to form a calcined residue;
    (E) grinding the calcined residue into a powder;
    (F) pelletizing the powder to form pellets; and
    (G) contacting the pellets with HF under conditions sufficient to convert the one or more of the hydroxide, the oxide, or the carbonate of the bivalent metal to a bivalent metal to a bivalent metal oxyfluoride.

11. The method of claim 10, wherein removing the water comprises driving off a portion of the solvent from the slurry to form a paste and drying the paste to form the solid residue.

12. The method of claim 10, wherein calcining takes place in N$_2$ flow for about 2 to about 8 hours at a temperature from about 300° C. to about 600° C.

13. The method of claim 10, wherein the solid residue is ground to a finely divided powder.

14. The method of claim 10, wherein the bivalent metal oxyfluoride is represented by the following:

$$n \text{ wt. } \% \text{ MX/M'O}_y\text{F}_z$$

wherein the alkali metal halide is represented by MX; wherein the bivalent metal oxyfluoride is represented by MX/M'O$_y$F$_z$; wherein 0<y<1 and 0<z<2 and wherein y+z/2=1; wherein M is an alkali metal ion selected from the group consisting of Li$^+$, Na$^+$, K$^+$, Rb$^+$, and Cs$^+$, X is a halogen ion selected from the group consisting of $F^-$, $Cl^-$, $Br^-$, and $I^-$, M' is a bivalent metal ion; wherein n is a weight percentage of about 0.05% to about 50% MX based on the total weight of the MX and $M'O_yF_z$, and wherein y and z are the mole fractions of oxygen and fluorine in $M'O_yF_z$, respectively.

15. The method of claim 14, wherein the bivalent metal is selected from the group consisting of $Mg^{2+}$, $Ca^{2+}$, $Sr^{2+}$, $Ba^{2+}$, $Ni^{2+}$, $Fe^{2+}$, $Co^{2+}$, $Cu^{2+}$, and $Zn^{2+}$, wherein the halide ion is selected from the group consisting of $F^-$ and $Cl^-$.

16. The method of claim 14, wherein the bivalent metal ion is $Mg^{2+}$ or $Ni^{2+}$, wherein the alkali metal ion is $Cs^+$ or $K^+$, and wherein the halogen ion is selected from the group consisting of $F^-$ and $Cl^-$.

17. The method of claim 10, wherein the pellets are contacted with HF for about 0.5 to about 20 hours at a temperature from about 300° C. to about 600° C.

18. The method of claim 9, further comprising
(C) extruding the slurry to form an extrudate;
(D) substantially removing the solvent from the extrudate to form a solid residue of the an alkali metal halide and the one or more of the hydroxide, the oxide, or the carbonate of the bivalent metal;
(E) calcining the solid residue at conditions sufficient to effect substantial calcination to form a calcined residue;
(F) grinding the calcined residue into a powder;
(G) pelletizing the powder to form pellets; and
(H) contacting the pellets with HF under conditions sufficient to convert the one or more of the hydroxide, the oxide, or the carbonate of the bivalent metal to a bivalent metal to a bivalent metal oxyfluoride.

\* \* \* \* \*